United States Patent [19]

Hamer

[11] Patent Number: 4,957,667

[45] Date of Patent: Sep. 18, 1990

[54] METHOD OF REDUCING SURFACE DEFECTS IN A POSITIVE DENTAL MODEL

[75] Inventor: James D. Hamer, White Bear Lake, Minn.

[73] Assignee: Minnesota Mining and Manufacturing Company, St. Paul, Minn.

[21] Appl. No.: 268,258

[22] Filed: Nov. 7, 1988

[51] Int. Cl.$^5$ .............................................. B28B 7/36
[52] U.S. Cl. ...................................... 264/16; 264/19; 264/338; 427/133
[58] Field of Search ................... 264/16, 17, 18, 19, 264/20, 338; 427/133; 433/202.1

[56] References Cited

U.S. PATENT DOCUMENTS

| | | |
|---|---|---|
| 2,632,013 | 3/1953 | Wagner et al. . |
| 4,035,453 | 7/1977 | Hittmair et al. . |
| 4,060,897 | 12/1977 | Greenstein ..................... 264/19 X |
| 4,273,902 | 6/1981 | Tomioka et al. . |
| 4,359,565 | 11/1982 | Puppe et al. . |
| 4,401,498 | 7/1983 | Jahn et al. ........................ 264/16 X |
| 4,657,959 | 4/1987 | Bryan et al. . |
| 4,806,575 | 2/1889 | Waller et al. ...................... 523/120 |

FOREIGN PATENT DOCUMENTS 2262955 3/1975 France .
2400052 8/1978 France .

OTHER PUBLICATIONS

Ullmann's Encyclopedia of Industrial Chemistry, Fifth, Completely Revised Edition, vol. A 5: Cancer Chemotherapy to Ceramic Colorants, 1986: pp. 313, 334–335, 342, 344, 350–351.

Ullmanns Encyklopadie der technischen Chemie Hormone bis Keramik, Katalyse und Katalysatoren, pp. 533–534 (No translation).

*Primary Examiner*—Jan H. Silbaugh
*Assistant Examiner*—Christopher A. Fiorilla
*Attorney, Agent, or Firm*—Wegner & Bretschneider

[57] ABSTRACT

A method of making a positive model of a tooth or gum including the steps of pouring hardenable positive impression material into a negative impression of the tooth or gum comprising a cured, vinyl polysiloxane composition, and hardening the positive impression material, and further including applying finely divided palladium over at least part of the surface of the negative impression that will contact the positive impression material before pouring the hardenable positive impression material.

10 Claims, No Drawings

METHOD OF REDUCING SURFACE DEFECTS IN A POSITIVE DENTAL MODEL

This invention relates to a method of making a positive dental model and materials useful in said method. In particular, it relates to a method of making a positive dental model based on a negative impression made from a cured vinyl polysiloxane composition.

In modern dentistry, models are made of patient's teeth for a variety of reasons, e.g., to make tooth crowns. In one such method, curable vinyl polysiloxane compositions are used to make negative impressions of teeth, which serve as molds for casting the positive model, the positive model being a cured epoxy or gypsum material. However, after pouring the curable material into the negative impression mold thus formed, hydrogen gas escaping from the cured mold causes pits to form in the curable material before it has a chance to set, resulting in imperfect positive models Accordingly, the present invention is an improvement in a method for making a positive model of a tooth or gum comprising the steps of pouring hardenable positive impression material into a negative impression comprising a cured, vinyl polysiloxane composition and hardening the positive impression material, the improvement comprising applying finely divided palladium to at least part of the surface of the negative impression that will contact the positive impression material before pouring the hardenable positive impression material. The present invention alternatively comprises mixing finely divided palladium with the positive impression material prior to pouring.

Vinyl polysiloxane compositions used to make a negative impression of a tooth or gum are well known. Preferably, the compositions are two-part self-addition-cured compositions. Examples of useful compositions are disclosed in U.S. Pat. Nos. 3,950,330 (Hittmair), 4,657,959 (Bryan), and "Silicones," *KirkOthmer Encyclopedia of Chemical Technology*, No. 3rd, Ed. 20, 922–962 (1982), the disclosures of which are incorporated herein by reference. Other useful compositions will be apparent to those having ordinary skill in the art.

Techniques for forming the negative impression are well known. These techniques involve applying the composition to the tooth, allowing the composition to cure, and removing the negative impression, commonly referred to as a "single phase" technique. Advantageously, a similar, but more heavily filled, curable composition is applied over the cured or uncured first-applied composition, a technique known as a "putty wash," which provides efficient use of critical materials and additional cost savings.

In one embodiment of the present invention, finely divided palladium, preferably having a particle size less than about 100 microns, is applied dry to the surface of a negative impression. Preferably, the amount of palladium used is at least about 0.0001 g/cm$^2$ of impression surface area, more preferably between 0.0001 and 0.10 g/cm$^2$. Palladium alloyed with other hydrogen-scavenging metals or adsorbed on a solid substrate such as carbon, alumina, or calcium carbonate, is also useful. More preferably, palladium is applied as a particulate suspension, the suspending material facilitating distribution over the impression surface. Preferably, the suspending material comprises either a solvent having a vapor pressure greater than about 0.09 1/M, more preferably greater than 0.2 1/M, or a solvent having a surface tension at 20° C. less than about 23.0 dynes/cm. Examples of solvents having the requisite surface tension include silicone oils and silicone polymers, such as trimethylsiloxy-terminated polydimethylsiloxanes, as well as ammonia, chlorine, ethyl mercaptan, hexane, hydrogen peroxide, and methyl alcohol. Useful solvents having the required vapor pressure include organic solvents such as toluene, acetone, heptane, and hexane. Other useful solvents will be apparent to those of ordinary skill in the art. The amount of palladium in suspension is preferably at least about 0.1% by weight of the suspension, more preferably between 0.1 and 10.0% by weight.

Optionally, surfactants and disinfectants are also useful in the suspension. Useful surfactants include those disclosed in the aforementioned U.S. Pat. No. 4,657,959 (Bryan). Useful disinfectants include gluteraldelydes.

After the palladium has been applied to the surface of the negative impression, the hardenable positive impression material is poured into the negative impression, cured, and removed to form the positive model. Suitable hardenable positive impression materials are well known and include materials such as aqueous gypsum slurries and thermosetting materials such as epoxy resins. Suitable epoxy resins include commercially available two-part epoxy materials.

In another embodiment of the present invention, finely divided palladium is mixed with the hardenable positive impression material before it is poured into the negative impression. For example, the palladium can be mixed dry with gypsum powder and then mixed with water and poured into the negative impression. Alternatively, the finely divided palladium is first mixed with the water before adding to the gypsum powder and then poured into the negative impression and allowed to set. When mixed either wet or dry with the gypsum powder, the amount of palladium is preferably at least about 0.05%, more preferably between 0.1 and 1.0%, by weight of gypsum powder. Optionally, a disinfectant, surfactant, or mixture thereof such as disclosed hereinabove are also added. Preferably, when mixed first with water, the aqueous palladium suspension is sonically dispersed before adding to the gypsum powder.

To more clearly describe the present invention, the following non-limiting examples are provided. In the examples, all parts and percentages are by weight unless otherwise indicated.

EXAMPLE 1

A negative impression of teeth is made from a curable two-part composition having the following formulation:

A catalyst part comprising vinyl-terminated polydimethyl siloxane, $M_n$-24000, at 46.3 percent, silicone-treated silica ("QUSO 545," Philadelphia quartz), at 6.1 percent, ground silica ("IMSIL A-25," Illinois Materials), at 46.9 percent, and a catalyst made from a 2:1 mixture of 1, 3-divinyl tetramethyl disiloxane and chloroplatinic acid, at 0.7 percent; a base part comprising vinyl-terminated polydimethyl siloxane, $M_n$-24000 at 42.4 percent, silicone-treated silica at 7.3 percent, ground silica at 46.6 percent, silicone cross linking agent (copolymer based on monomers charged having an average composition $MD'_{10}D_{21}M$ where $M=Si(CH_3)_3O_{0.5}$, $D=Si(CH_3)_2O$, and $D'=Si(CH_3)HO$). A polyalkylene oxide modified polymethyl siloxane surfactant ("SILWET L-77," Union Carbine Corp.), is added to each part at a level of one percent. The two parts are then combined in equal proportions, rapidly mixed, and applied to a dentiform model to make a negative impression. After curing, the negative impression is removed from the dentiform model and a 0.1 percent palladium powder (palladium black, available from Alfa Products, Danvers, Mass.) suspension in toluene is brushed onto the surface of the negative impression in an amount sufficient to wet the entire surface, which is then allowed to dry.

A gypsum slurry containing 23 parts water and 100 parts gypsum powder is poured into the negative impression and allowed to set. The positive model is removed from the mold and shows no visible pitting.

As a control, the above procedure is repeated, but no palladium powder suspension is applied to the negative impression surface. The resulting cured positive model shows numerous pits.

EXAMPLE 2

A negative impression of teeth is prepared as in Example 1 (A palladium suspension was not brushed on the model). A gypsum slurry is prepared by combining 100 parts gypsum powder with a sonically dispersed suspension of 0.062 parts palladium powder and 23 parts water. The slurry is poured into the negative impression, allowed to cure, and removed. No visible pits are observed.

EXAMPLE 3

A positive model is prepared as in Example 2, but 0.01 percent (based on the water) of a polyalkylene oxide modified polymethyl siloxane surfactant is added to the sonically dispersed suspension before mixing with the gypsum powder. The positive model shows no visible pitting.

EXAMPLE 4

A positive model is prepared as in Example 2, but 1.0 percent (based on the water) of a glutaraldehyde disinfectant is added to the sonically dispersed suspension before mixing with the gypsum powder. No pits are observed in the positive model.

EXAMPLE 5

A negative impression is made as in Example 1 (A palladium suspension was not brushed on the model). A gypsum slurry is prepared by combining a dry mix of 0.1 parts palladium powder and 100 parts gypsum powder with 23 parts water. After pouring into the negative impression and allowing it to set, the positive model shows no visible pitting.

Claimed is:

1. In a method of making a positive model of a tooth or gum comprising the steps of pouring hardenable positive impression material into a negative impression of the tooth or gum comprising a cured, vinyl polysiloxane composition, and hardening the positive impression material, the improvement comprising providing for scavinging of hydrogen gas escaping from the negative impression after pouring of the harden able positive impression material by applying finely divided palladium over at least part of the surface of the negative impression that will contact the positive impression material before pouring the hardenable positive impression material.

2. The method of claim 1 wherein the palladium is applied as a particulate suspension.

3. The method of claim 2 wherein the suspending material is a solvent having a vapor pressure greater than about 0.09 1/M.

4. The method of claim 2 wherein the suspending material is toluene.

5. The method of claim 2 wherein the suspending material has a surface tension at 20° C. less than about 23 dynes/cm.

6. The method of claim 2 wherein the suspending material is a silicone oil or silicone polymer.

7. The method of claim 2 using at least about 0.1 percent palladium by weight of suspension.

8. The method of claim 1 using at least 0.0001 g. palladium per $cm^2$ of impression surface.

9. The method of claim 1 wherein the palladium is applied dry.

10. The method of claim 1 wherein the palladium has a particle size less than about 100 microns.

* * * * *